(12) United States Patent
Schlimper et al.

(10) Patent No.: US 9,949,804 B2
(45) Date of Patent: Apr. 24, 2018

(54) ORTHODONTIC BRACKET AND A METHOD OF MAKING AN ORTHODONTIC BRACKET

(71) Applicant: 3M INNOVATIVE PROPERTIES COMPANY, St. Paul, MN (US)

(72) Inventors: Ralf Schlimper, Melle (DE); Ralf M. Paehl, Melle (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/911,705

(22) PCT Filed: Aug. 13, 2014

(86) PCT No.: PCT/US2014/050940
§ 371 (c)(1),
(2) Date: Feb. 11, 2016

(87) PCT Pub. No.: WO2015/023784
PCT Pub. Date: Feb. 19, 2015

(65) Prior Publication Data
US 2016/0199154 A1    Jul. 14, 2016

(30) Foreign Application Priority Data
Aug. 14, 2013    (EP) ..................................... 13180393

(51) Int. Cl.
*A61C 3/00*    (2006.01)
*A61C 7/00*    (2006.01)
(Continued)

(52) U.S. Cl.
CPC .............. *A61C 7/002* (2013.01); *A61C 7/145* (2013.01); *A61C 7/16* (2013.01)

(58) Field of Classification Search
CPC .. A61C 7/146; A61C 7/16; A61C 7/14; A61C 7/12; A61C 7/002; A61C 7/145
(Continued)

(56) References Cited

U.S. PATENT DOCUMENTS 5,607,301 A * 3/1997 Roman ................. A61C 7/146
433/8
9,662,055 B2    5/2017 Hoss et al.
(Continued)

FOREIGN PATENT DOCUMENTS

CN    101284302    10/2008
CN    101647729    2/2010
(Continued)

OTHER PUBLICATIONS

Written Opinion of the ISA. PCT/US2014/050940. Filed Aug. 13, 2014.*
(Continued)

*Primary Examiner* — Yogesh Patel (57) ABSTRACT

Method of making a customized orthodontic bracket. A bracket receiving area is determined on a three-dimensional tooth model of a patient's tooth, and a bracket base is provided with a tooth-facing surface that is shaped according to the shape of the bracket receiving area. An outline of a bracket head is determined on the tooth model, and the bracket head is provided with a bracket head surface that is shaped according to the shape within the bracket head outline. The bracket has an outer surface with a shape corresponding to the natural shape of the patient's tooth, which helps to minimize discomfort during orthodontic treatment with the brackets.

15 Claims, 4 Drawing Sheets

(51) Int. Cl.
*A61C 7/14* (2006.01)
*A61C 7/16* (2006.01)

(58) Field of Classification Search
USPC .......................................... 433/8–22
See application file for complete search history.

(56) References Cited

U.S. PATENT DOCUMENTS

2010/0324715 A1   12/2010  Yang
2012/0015315 A1*   1/2012  Wiechmann ........... A61C 7/002
                                                                             433/8

FOREIGN PATENT DOCUMENTS

EP           1474064        11/2004
WO    WO 2001-80761       11/2001
WO       WO 0180761 A2 *  11/2001    ............... A61C 7/00

OTHER PUBLICATIONS

International search report for PCT International Application No. PCT/US2014/050940 dated Nov. 18, 2014, 4 pages.

* cited by examiner

ORTHODONTIC BRACKET AND A METHOD OF MAKING AN ORTHODONTIC BRACKET

CROSS REFERENCE TO RELATED APPLICATIONS

This application is a national stage filing under 35 U.S.C. 371 of PCT/US2014/050940, filed Aug. 13, 2014, which claims the benefit of European Application No. 13180393.4, filed Aug. 14, 2013, the disclosures of which are incorporated by reference in their entirety herein.

FIELD OF THE INVENTION

The disclosure relates to a method of making a customized orthodontic bracket which comprises a bracket base for attaching the bracket at a patient's tooth, a bracket body and an archwire slot, and in particular to a method of making such a bracket with a bracket body that exhibits an outer surface of a shape corresponding to the shape of the tooth for which the bracket is customized. The disclosure further relates to a bracket that is obtainable by the method of the disclosure and a kit comprising a plurality of brackets of the disclosure.

BACKGROUND ART

Orthodontic brackets are generally used in orthodontic treatments for moving one or more teeth from an initial position to a desired position in a patient's dentition. The initial position typically refers to a position at the beginning of an orthodontic treatment, for example a position in which the labial faces of the teeth are misaligned to each other, whereas in the desired position the labial faces of the same teeth may be generally aligned. For example the patient's teeth may be aligned relative to each other to provide the dentition with a more aesthetically pleasant appearance. Further one or more teeth may be moved within the dentition to compensate for a malocclusion. Such a movement of a tooth or teeth can be typically achieved by using one or more brackets attached to one or more teeth. The brackets are typically connected to an elastic archwire for applying a force to the teeth toward the desired position over a longer term.

Often orthodontic brackets are off-the-shelf products which are designed to for use with clinical situations of different patients. Further there are customized orthodontic brackets which are typically made to fit with an individual clinical situation of one particular patient.

For example US 2012/0015315 A1 discloses a customized orthodontic bracket system which includes a bracket having a customized bracket bonding pad for bonding the bracket to a tooth of a patient and a bracket slot adapted to receive a customized archwire. The customized archwire is adapted to be positioned in the bracket slot to form a precise bracket slot-archwire interface.

Although a variety of different brackets and bracket systems are on the market there is still a desire to provide brackets which on the one hand match an individual clinical situation and on the other hand are minimized in costs for manufacturing and costs for application to a patient's teeth. Further such brackets desirably can be placed easily and precisely to a patients teeth, and further are desirably sufficiently durable over the time period of an orthodontic treatment.

SUMMARY OF THE INVENTION

The disclosure relates to a customized orthodontic bracket and a method of making a customized orthodontic bracket. In particular the customized orthodontic bracket of the disclosure is preferably adapted for an attachment to the lingual side of a patient's tooth, although the same disclosure can be used to provide a customized bracket that is adapted for attachment to the labial side of a patient's tooth.

The bracket as concerned with the disclosure comprises a bracket base for attaching the bracket at a patient's tooth, a bracket body and an archwire slot. The bracket body extends from the bracket base in a dimension of a bracket height. The bracket slot is typically arranged within the bracket body. The bracket body further forms a bracket head adjacent a free end of the bracket body. The free end of the bracket body typically also forms a free end of the bracket, in particular in a situation in which the bracket is attached to a patient's tooth. Such free end of the bracket typically faces away from the bracket base. Accordingly the free end of the bracket or the bracket body forms the tongue-facing end or the cheek-facing end of the bracket, depending on whether the bracket is attached to the lingual or labial side, respectively, of the patient's tooth.

The bracket head forms a ligating portion which, with respect to another bracket body portion, forms a projection in a dimension of a bracket width. The ligation portion typically is adapted to attach a so-called ligature, typically an elastic band or ring, to the bracket. Further the ligation portion is typically adapted such that the ligature can be attached at opposite sides of the slot and in a position to span the slot generally transverse a path along which the slot extends through the bracket or generally transverse a path along which the archwire runs. Thus the ligature can be used to affix an archwire placed in the slot to the bracket.

For the purpose of the present specification the term "thickness" refers to one dimension in a three-dimensional Cartesian coordinate system, whereas the term "width" refers to the remaining other two dimensions in the same coordinate system.

The method for making the customized orthodontic bracket as described herein comprises the steps of:
- providing a three-dimensional tooth model representing the shape of at least part of a patient's tooth;
- determining a bracket receiving area on the tooth model;
- providing the bracket base with a tooth-facing surface that is shaped according to the three-dimensional shape of the bracket receiving area;
- determining an outline of the bracket head on the tooth model; and
- providing the bracket head with a bracket head surface that is shaped according to the three-dimensional shape within the bracket head outline.

It is presently preferred that the three-dimensional tooth model representing the shape of at least part of a patient's tooth is provided in the form of a three-dimensional computer representation. The tooth model may define a three-dimensional outer surface of the tooth, for example in the form of a plurality of three-dimensional coordinates and/or a three-dimensional virtual wire frame.

The bracket receiving area as referred to herein preferably corresponds to the footprint of a bracket appropriately attached to the patient's tooth. The bracket receiving area further may refer to the actual physical area of the patient's tooth, an area on a physical model of the patient's tooth, and preferably an area on a virtual model of the patient's tooth.

The bracket receiving area and/or the bracket head outline may be determined directly on the tooth model or on a copy of the tooth model. The skilled person will recognize that either or both, the bracket receiving area and/or the bracket head outline, may be determined on a physical model and converted into a virtual (computer processable) bracket receiving area and/or the bracket head outline. One way of determining the bracket receiving area and/or the bracket head outline may comprise the marking of an area on a physical model, for example using a color pen, scanning the physical model and recognizing the marking, for example by contrast evaluation, by computer aid.

The disclosure is advantageous in that it helps providing customized orthodontic brackets which are minimized in thickness and which further provide a relatively high comfort for a patient undergoing a treatment with such brackets. In particular the disclosure helps minimizing the time period a patient requires to get used to the brackets after they have been freshly attached to the patient's tooth. It has been found that particularly the natural tooth shape comprised within the shape of the free end of the bracket contributes in maximizing such comfort for the patient.

The method of the disclosure may further comprise the step of three-dimensionally scanning at least a portion of a patient's dentition.

In one embodiment the bracket receiving area is determined by drawing several points or at least one line on the tooth model by use of a CAD (Computer Aided Design) system. The points may be used to define a (preferably closed) spline on the tooth model, and that spline may define the outline of the bracket receiving area. Further the at least one line may be closed and define the outline of the bracket receiving area.

In a presently preferred embodiment the tooth-facing surface and the head surface face away from each other.

In one embodiment the method comprises the steps of:
deriving the tooth-facing surface from the bracket receiving area (or a copy thereof) in the form of a three-dimensional computer representation;
providing an offset of the tooth-facing surface to form a rear surface of the bracket base in the form of a three-dimensional computer representation; and
providing a circumferential side wall extending between the outer boundaries of the tooth-facing surface and the rear surface, and thereby providing the bracket base in the form of a three-dimensional computer representation.

The rear surface may be derived from the bracket receiving area (or a copy thereof). Further the offset is preferably a parallel offset such that the tooth-facing surface and the rear surface are equidistantly spaced. The offset may be selected such that the thickness of the bracket base is between about 0.4 mm and about 1 mm, preferably about 0.5 mm. The method may further comprise the step of rounding the edge formed between the rear surface and the circumferential wall of the bracket base, for example by a radius. A typical size of a radius is between 0.2 mm and 0.8 mm.

In a further embodiment the method comprises the step of obtaining a standardized bracket body from a library holding a plurality of different standardized bracket bodies. The standardized bracket bodies are preferably provided in the form of a three-dimensional computer representation. The method may further comprise the steps of positioning and orienting the bracket body relative the bracket base and merging the bracket body and the bracket base to the bracket. Further the method may comprise the step of modifying the standardized bracket body, for example adding, reorienting or repositioning a bracket slot or trimming the standardized bracket body.

In one embodiment the ligating portion forms at least one tie wing. The ligating portion may further form at least one hook. In preferred embodiments the ligating portion forms a pair of tie wings which are arranged opposed to each other, or two pairs of such tie wings. A bracket for a relative small incisal tooth may for example have one pair tie wings, whereas a bracket for a molar tooth may have two pairs of tie wings. One or more hooks may be provided in addition or instead on any tie wing. According to the disclosure at least one surface of the tie wing is provided with a three-dimension shape which corresponds to the three dimensional shape of the tooth for which the bracket is customized.

In a further embodiment the method comprises the step of providing the bracket head in dimensions of the bracket width with an outer shape that corresponds to the bracket head outline. In this regard the method may further comprise the steps of:
determining a preliminary bracket head outline in a virtual plane; and
projecting the preliminary bracket head outline on the tooth model (or a copy or partial copy of the tooth model), and thereby determining the bracket head outline.

The preliminary bracket head outline may be obtained from a library holding a plurality of different preliminary bracket head outlines. Such preliminary bracket head outlines may be based on brackets having ligating portions forming one, two, three or four tie wings for example. A user of the method of the disclosure may select the appropriate preliminary bracket head outline based on the number of desired tie wings, for example.

In a further embodiment the method comprises the step of modifying the preliminary bracket head outline by a user using CAD.

The projection is preferably an orthogonal projection onto an averaged plane of the bracket receiving area. Such an averaged plane has an angle in the three-dimensional coordinate system which is averaged based on the overall three-dimensional angle of the bracket receiving surface in the same coordinate system.

In one embodiment the bracket head outline on the tooth model is located and sized to overlap with the bracket receiving surface. The overlap between the area defined by the bracket head outline relative to the bracket receiving surface is preferably at a ratio of at least 50%, more preferably at least 85%.

In a further embodiment the method comprises the step of creating an offset of an area on the tooth model which is defined by the bracket head outline. The offset is preferably used as the bracket head surface or copied to create the bracket head surface. The bracket head surface may be positioned relative to the bracket body by a user and/or by computer aid. For example the bracket head surface may be positioned with a coordinate defining the bracket head surface on a coordinate defining a surface of the standardized (eventually modified) bracket body, or the bracket head surface may be placed at a desired offset selected by the user and used to trim off such portions of the standardized bracket body which protrude over the bracket head surface.

In one embodiment the method comprises the steps of:
performing a (potentially virtual) treatment planning in which the position and orientation of the patient's tooth at an initial position and a desired position is determined;
determining an archwire shape and position relative to several teeth of the same patient in the desired position of the tooth; and
providing the archwire slot of the bracket in appropriate position and orientation of the archwire shape and position.

The archwire in presently preferred circumstances has a generally rectangular cross-section and extends generally U-shaped at that cross-section. Accordingly the treatment planning may be performed in that the position and orientation of several or all of the patient's teeth at an initial position and a desired position are determined, and the archwire shape and position may be determined relative to several or all teeth of the patient in the desired position of such teeth. This further allows for providing the archwire slot of several brackets in appropriate position and orientation of the archwire shape and position. The skilled person will recognize that the archwire shape and position may be determined relative to several teeth of the patient also accounting for the initial position of the tooth. Thus it may be made sure that one or a minimized amount of different archwires can used during the whole orthodontic treatment.

In a further embodiment the method comprises the steps of:
providing the shape of the bracket in the form of computer processable data; and
using the bracket data to manufacture the bracket, preferably in one piece, by an automated manufacturing process.

Such computer processable data may comprise CAD or STL data as they can be processed by an automated manufacturing machine. Preferably the automated manufacturing comprises a build-up or rapid prototyping process in which the bracket is built up successively but in which the built up bracket finally forms one contiguous piece. Such a manufacturing process may for example comprise wax printing, powder printing, Stereo Lithography or Selective Laser Melting. In a preferred embodiment the entire bracket is preferably made (directly from the computer processable data) by Selective Laser Melting.

In a further aspect the disclosure relates to a customized orthodontic bracket which is obtainable by the method of the disclosure.

In still a further aspect the disclosure relates to a customized orthodontic bracket which comprises:
a bracket base for attaching the bracket at a patient's tooth,
a bracket body and
an archwire slot for receiving an archwire therein,
the bracket body extending from the bracket base in a dimension of a bracket height and forming a bracket head adjacent a free end of the bracket body,
the bracket head forming a ligating portion which, with respect to another bracket body portion, forms a projection in a dimension of a bracket width; the bracket further comprising:
at the bracket base a tooth-facing surface that is shaped according to a bracket receiving area having a three-dimensional shape in accordance with a three-dimensional shape of a patient's tooth; and
at the head portion a bracket head surface that is shaped according to an area defined by a bracket head outline and having a three-dimensional shape in accordance with a three-dimensional shape of the same patient's tooth.

Thus the bracket of the disclosure may have two opposite outer surfaces, the bracket head surface and the tooth-facing surface, which have the shape of the natural tooth the bracket is customized for. In case the bracket base has a rear surface which is shaped in accordance to the tooth-facing surface, the bracket of the disclosure thus has three outer surfaces which have the shape of the natural tooth the bracket is customized for.

In an embodiment the customized orthodontic bracket is made of a material selected from gold, titanium alloy, and stainless steel, preferably a cobalt-chromium steel.

In a further aspect the disclosure relates to a kit of customized orthodontic brackets according the disclosure. The brackets are assigned and shaped to each match with a different particular tooth of the same patient's dentition. The kit further comprises at least one archwire adapted for running through the slots of the brackets attached to the patient's teeth.

DETAILED DESCRIPTION OF THE DISCLOSURE

Figure 1:
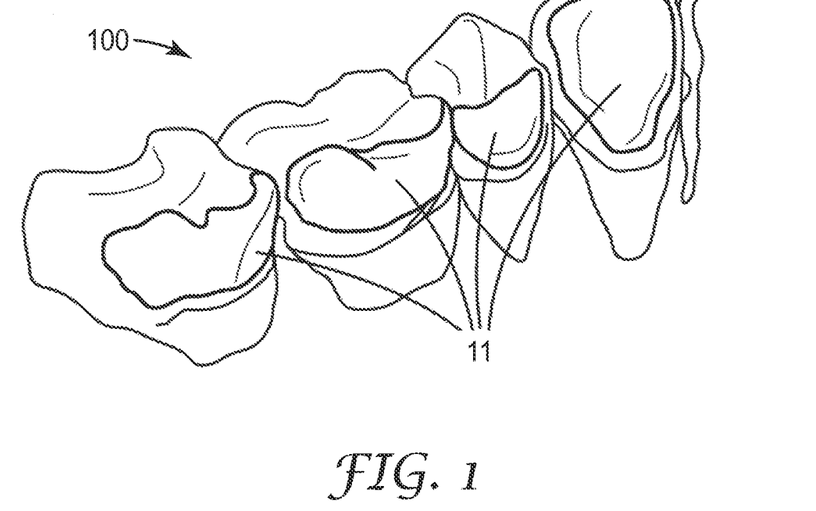
FIG. 1 is a perspective view illustrating the determination of a bracket receiving area according to an embodiment of the disclosure.

FIG. 1 shows a three-dimensional computer representation or tooth model 100 of a portion of a patient's dentition. The tooth model 100 is based on a cloud of three-dimensional coordinates defining points of the outer surface or shell of the patient's dentition. The tooth model 100 shown can be displayed on a computer screen of a CAD system in the form of a wire frame model, in which the coordinates form corners of small triangles. Or the tooth model 100 shown may be displayed as a rendering in the form of a contiguous and shaded (optionally colored as a false color rendering) virtual shell through the (invisible) coordinates.

A tooth model of the patient's teeth can be obtained from scanning a positive or negative physical model of the patient's teeth, for example a plaster model or a dental impression taken from the patient's teeth. A suitable scanner is for example provided in a system available under the designation LAVA™ Design Systems, from 3M Deutschland GmbH, Germany. Alternatively, the tooth model may be obtained by an scanning the patients teeth in vivo with an intraoral scanner, such as the 3M True Definition Scanner available from 3M Company, St. Paul, Minn.

A plurality of bracket receiving areas 11 are arranged on the tooth model 100. The bracket receiving areas 11 are determined with computer aid by a user directly on the tooth model 100. The skilled person will recognize however that the bracket receiving areas 11 may be determined on a copy of the tooth model 100 or provided otherwise, for example by upload, scanning, or in any other appropriate way. In the example the outline of the bracket receiving areas 11 are obtained from a spline drawn based on user-defined points on the tooth model 100. For example the user may click on certain points on the tooth model 100 and the CAD system may automatically create the spline based thereon to create the outline of the bracket receiving area. The CAD system preferably has functionality to determine the size of the bracket receiving area and to provide a warning to the user in case the bracket receiving area is too small, for example to make sure that the area is sufficiently large to provide a good bond between the finished bracket and the patient's tooth. Further the CAD system may have functionality to suggest a minimum bracket receiving area, for example in the form of a circle on the tooth model 100, and the user may extend the suggested bracket receiving area as required. Typically the bracket receiving area is designed large enough to cover portions of the tooth surface having a significant curvature. Thus the finished bracket can be easily "snapped" into the appropriate position on the tooth in which the bracket base matches in shape with the tooth surface.

The so defined bracket receiving area may be used to create a bracket base, for example by providing two copies of the bracket receiving area spaced parallel offset from each other. One of the copies may be used to create a virtual tooth-facing surface of the bracket base, whereas the other copy may be used as or to create a rear surface of the bracket pad. The gap between the tooth-facing surface and the rear surface may be closed by a three-dimensional wall extending circumferentially around the outlines of the tooth-facing surface and the rear surface. Further although the tooth-facing surface is overall shaped according to the three-dimensional shape of the bracket receiving area, the tooth-facing surface may additionally have a structure which is not present on the bracket receiving area or on the tooth model. For example the tooth-facing surface may comprise retention structures like a grid, mushroom pins or other appropriate structures. The tooth-facing surface may further comprise an encoding, for example a number, for identifying the bracket in relation to a particular tooth which the bracket is customized for.

In the example the bracket receiving area is used to define an averaged plane of that bracket receiving area. To derive the averaged plane a virtual perpendicular vector may be assigned to each of the smallest triangles formed by the coordinates defining the bracket receiving area. Because each of the triangles defines a virtual sub-plane the plurality of virtual perpendicular vectors can be virtually erected onto such sub-planes. From the plurality of so erected vectors, eventually being non-uniformly oriented, a resulting vector is determined by vector analysis, and the resulting vector is used to create the averaged plane as a perpendicular plane to the resulting vector.

Figure 2:
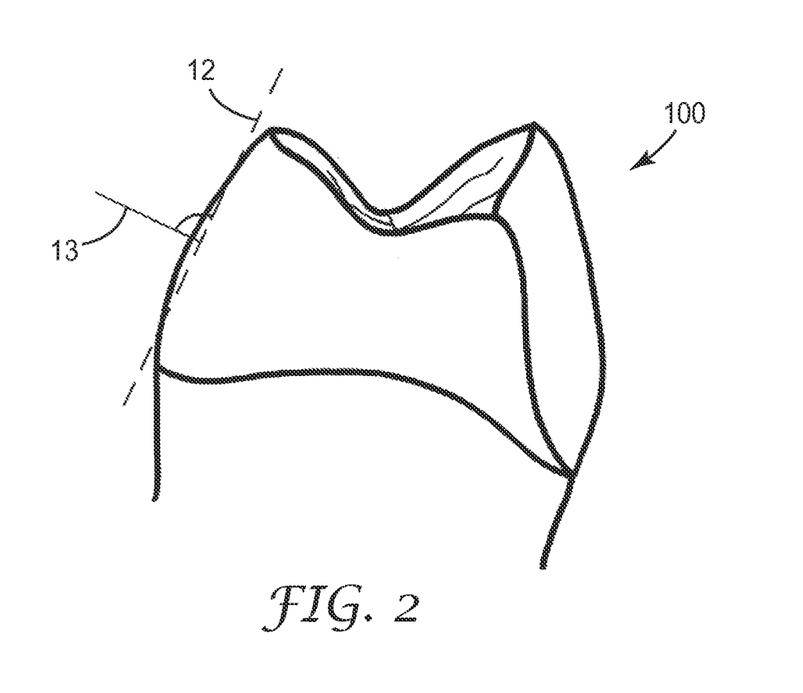
FIG. 2 is a perspective view illustrating the definition of an average plane according to an embodiment of the disclosure.

FIG. 2 shows such an averaged plane 12 defined on a tooth of the tooth model 100 and which is perpendicular to the resulting vector 13.

Figures 3, 3A:
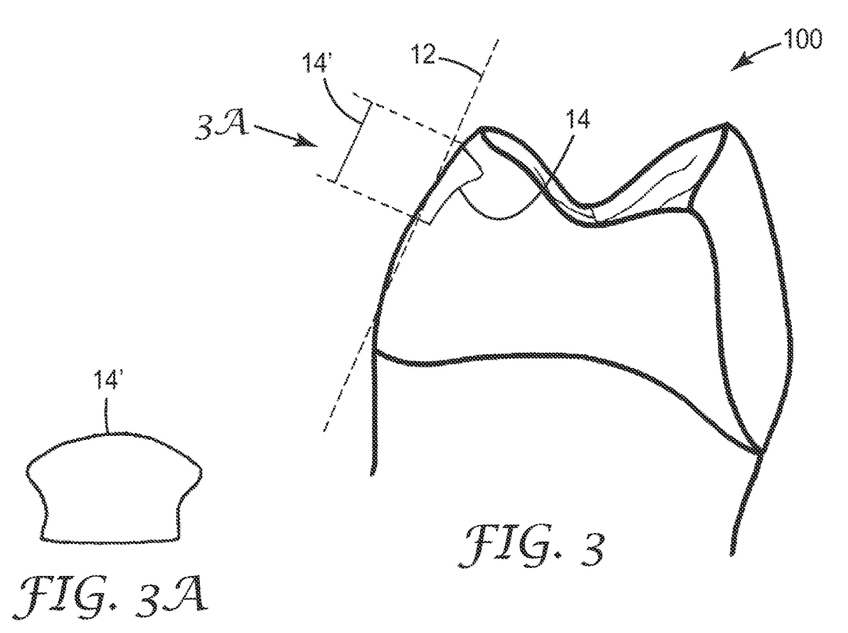
FIG. 3 is a perspective view illustrating the projection of a bracket head outline onto a tooth model according to an embodiment of the disclosure.
FIG. 3A is a top view of a preliminary bracket head outline as used in FIG. 3

In FIG. 3 the tooth model 100 is shown with an outline 14 of a bracket head determined on the tooth model 100. The bracket head outline 14 is determined by a projection of a preliminary bracket head outline 14' provided in the averaged plane 12 or a virtual plane which is parallel to the averaged plane 12. In the example the preliminary bracket head outline 14 is retrieved from a library holding a plurality of different preliminary bracket head outlines. The preliminary bracket head outlines in the library may be standardized and available for bracket types having one, two, three or four tie wings.

FIG. 3A shows such a standardized preliminary bracket head outline for defining the outer contour of a single tie wing for the bracket.

Figure 4:
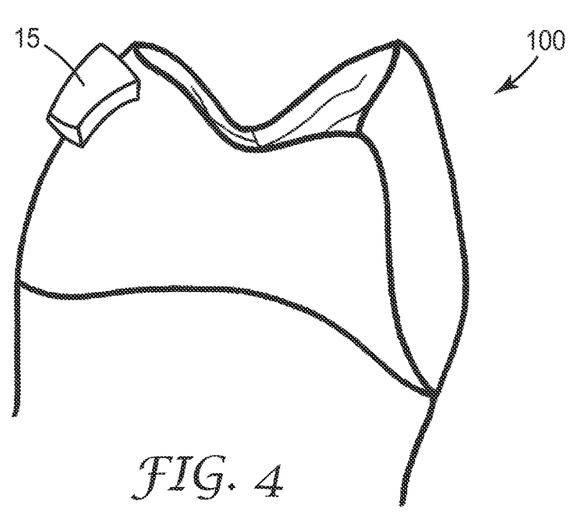
FIG. 4 is a perspective view illustrating the step of providing an offset the bracket head outline according to an embodiment of the disclosure.

FIG. 4 shows an offset 15 of the bracket head outline 14. The offset 15 is obtained from a parallel offset based on the averaged plane 12 (shown in FIG. 3). A tie wing may be created based on the offset 15 and the bracket head outline 14 in a similar manner as described for the bracket base above.

Figure 5:
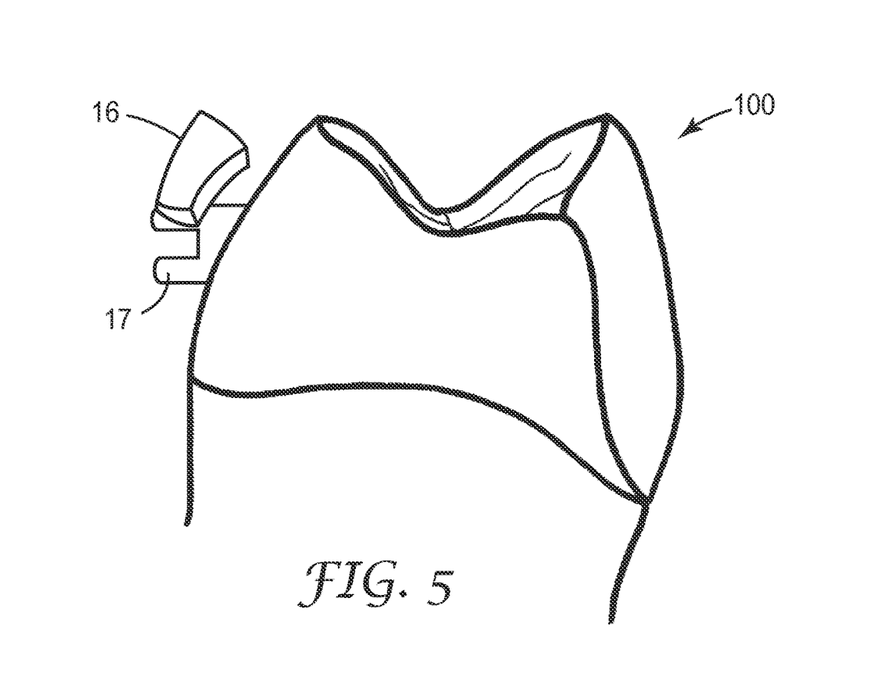
FIG. 5 is a perspective view illustrating the merger of a virtual tie wing and a virtual bracket body according to an embodiment of the disclosure.

FIG. 5 shows a (virtual) tie wing 16 positioned relative to a virtual bracket body 17. The bracket body 17 may be obtained from a library holding a plurality of different standardized bracket bodies. In the example the bracket body is positioned relative to the tooth model 100. Such position can be derived from a position of a virtual archwire located to a virtual model of the patient's dentition in the desired and/or the initial position. For example the archwire may be designed according to the so-called straight wire technique at a minimized distance to the lingual or labial sides of the teeth of the dentition. In the straight wire technique the archwire extends generally in a plane although it is curved in a U-shape. The slot of the virtual bracket body may be appropriately positioned relative to the archwire and the remainder of the body may be user-positioned such that the body extends substantially through a middle area of the bracket receiving area on the tooth model 100. A method of making a bracket by combining a virtual bracket body and a virtual bracket pad or base as it may be also used for the present disclosure is for example disclosed in more detail in EP 1 474 064 B1.

The tie wing 16 may be user-positioned (as illustrated) using CAD functionality. For example the tooth shaped surfaces of the tie wing 16 are preferably parallel offset from the corresponding area portions of the tooth model 100, whereas the three-dimensional position of the tie wing 16 may be determined by the user by moving the tie wing to a desired location. In other words the orientation of the tie wing 16 may be fixed whereas the three-dimensional position of the tie wing 16 may be variable. Further the fixation of the orientation of the tie wing 16 may be switchable on or off so that a change of the orientation is enabled to the user.

Once the tie wing 16 is appropriately positioned the tie wing 16 and the body 17 may be merged by computer aid. A further tie wing 17' (shown in FIG. 6) may be obtained in an identical manner.

Figure 6:
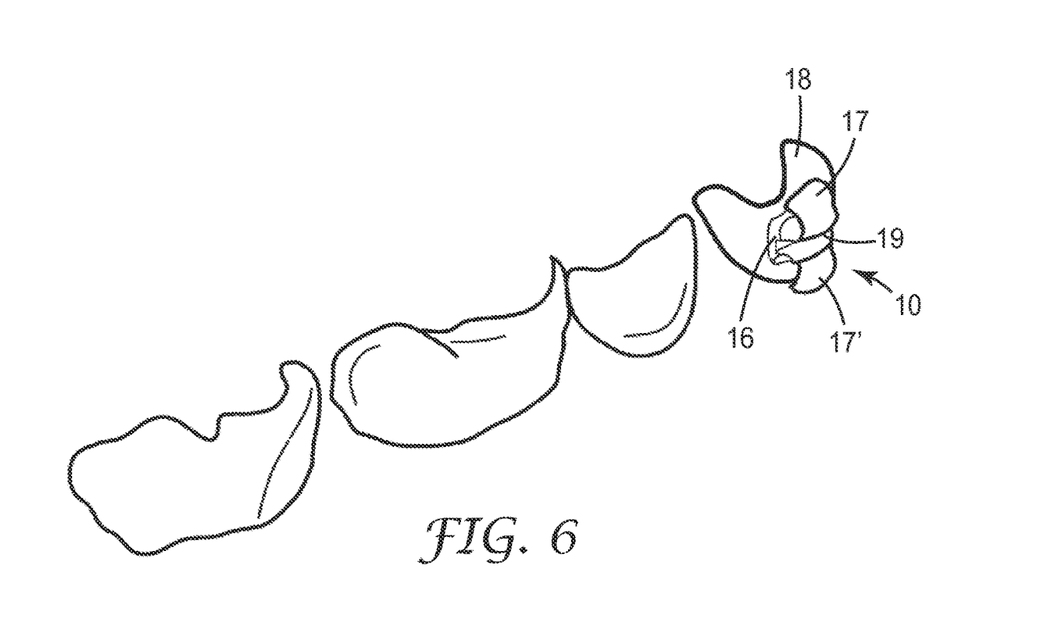
FIG. 6 is a perspective view of a virtual representation of the virtual bracket according to an embodiment of the disclosure.
Figure 7:
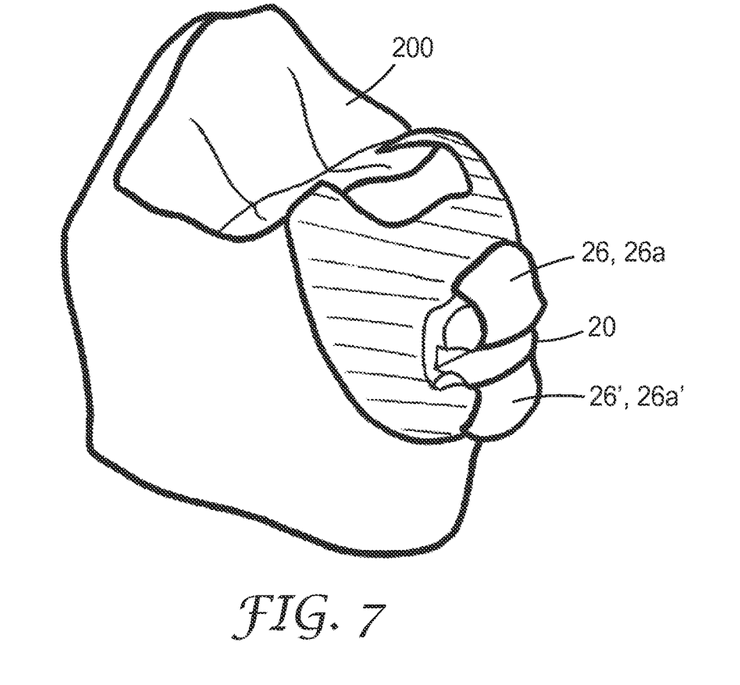
FIG. 7 is a perspective view of a physical bracket on a patient's tooth according to an embodiment of the disclosure.

FIG. 6 shows a virtual orthodontic bracket 10 having two tie wings 17, 17', a bracket base 18, a bracket body 16 and an archwire slot 19. The virtual orthodontic bracket 10 may be provided to a manufacturing machine in the form of computer processable data. Such a machine may be used to create the physical orthodontic bracket as shown in FIG. 7. Preferably the entire customized orthodontic bracket may be made as one single piece by use of Selective Laser Melting.

FIG. 7 shows the finished physical orthodontic bracket 20 attached to a patient's tooth 200. For attachment of the bracket 20 to the tooth 200 an adhesive or cement may be used. A suitable cement is for example available under the designation RelyX™ Unicem Self-Adhesive Resin Cement, from 3M Deutschland GmbH. As illustrated the tie wings 26, 26' exhibit bracket head surfaces 26a, 26a' which follow the shape of the tooth 20 in an area beneath the tie wings.

Thus the bracket of the disclosure helps minimizing any discomfort for the patient undergoing an orthodontic treatment.

Figure 8:
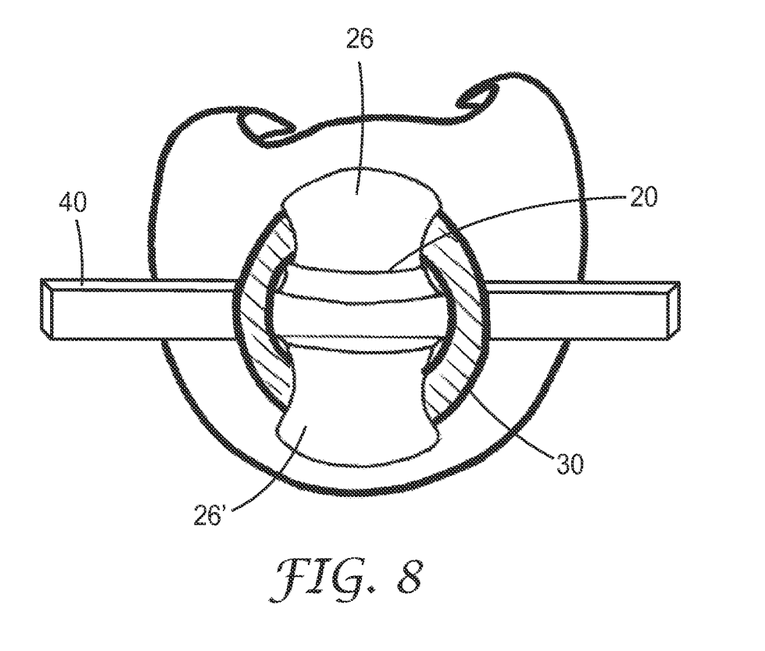
FIG. 8 is a further perspective view of a physical bracket on a patient's tooth according to an embodiment of the disclosure.

FIG. 8 shows a ligature 30 tied over the tie wings 26, 26a and affixing an archwire 40 to the bracket 20.

The invention claimed is:

1. A method of making a customized orthodontic bracket which comprises a bracket base for attaching the bracket at a patient's tooth, a bracket body and an archwire slot, the bracket body extending from the bracket base in a dimension of a bracket height and forming a bracket head adjacent a free end of the bracket body, the bracket head forming a ligating portion which, with respect to another bracket body portion, forms a projection in a dimension of a bracket width, the method comprising the steps of as executed by a computing device:

providing a three-dimensional tooth model representing the shape of at least part of a patient's tooth;

determining a bracket receiving area on the tooth model;

providing the bracket base with a tooth-facing surface that is shaped according to the three-dimensional shape of the bracket receiving area;

determining an outline of the bracket head on the tooth model; and providing the bracket head with a bracket head surface that is shaped according to the three-dimensional shape within the bracket head outline, wherein the bracket head forms a pair of opposed tie wings, each of the tie wings having a surface extending laterally from the bracket head over the tooth, wherein the laterally extending surfaces of the tie wings follow a shape of the tooth in an area beneath the tie wings.

2. The method of claim 1, wherein the tooth-facing surface and the bracket head surface face away from each other.

3. The method of claim 1, wherein the ligating portion forms at least one hook.

4. The method of claim 1, further comprising the step of providing the bracket head in dimensions of the bracket width with an outer shape that corresponds to the bracket head outline.

5. The method of claim 1, comprising the steps of:
determining a preliminary bracket head outline in a virtual plane; and
projecting the preliminary bracket head outline on the tooth model, and thereby determining the bracket head outline.

6. The method of claim 5, wherein the bracket head outline on the tooth model is located and sized to overlap with the bracket receiving surface.

7. The method of claim 6, wherein the overlap between the area defined by the bracket head outline relative to the bracket receiving surface is at a ratio of at least 50%.

8. The method of claim 6, further comprising the step of creating an offset of an area on the tooth model which is defined by the bracket head outline.

9. The method of claim 7, further comprising the step of creating an offset of an area on the tooth model which is defined by the bracket head outline.

10. The method of claim 5, further comprising the step of creating an offset of an area on the tooth model which is defined by the bracket head outline.

11. The method of claim 5, further comprising the step of providing the bracket head in dimensions of the bracket width with an outer shape that corresponds to the bracket head outline.

12. The method of claim 1 comprising the steps of:
determining the position and orientation of the patient's tooth at an initial position and a desired position as a part of a treatment plan;
determining an archwire shape and position relative to several teeth of the same patient in the desired position of the tooth; and
providing the archwire slot of the bracket in appropriate position and orientation of the archwire shape and position.

13. The method of claim 1 further comprising the steps of:
providing the shape of the bracket in the form of computer processable data; and
using the bracket data to manufacture the bracket by an automated manufacturing process.

14. The method of claim 13, wherein the manufacturing process comprises wax printing, powder printing, Stereo Lithography or Selective Laser Melting.

15. A customized orthodontic bracket, obtainable by the method of claim 1.

* * * * *